United States Patent [19]

O'Callaghan et al.

[11] 4,258,041
[45] Mar. 24, 1981

[54] (6R,7R)-7-[(Z)-2-(2-AMINOTHIAZOL-4-YL)-2-(2-CARBOXYPROP-2-OXYIMINO)ACETAMIDO]-3-(1-PYRIDINIUMMETHYL)-CEPH-3-EM-4-CARBOXYLATE AND SALTS THEREOF

[75] Inventors: Cynthia H. O'Callaghan, Gerrards Cross; David G. H. Livermore; Christopher E. Newall, both of London, all of England

[73] Assignee: Glaxo Group Limited, London, England

[21] Appl. No.: 42,594

[22] Filed: May 25, 1979

[30] Foreign Application Priority Data

May 26, 1978 [GB] United Kingdom ............... 22911/78
May 26, 1978 [GB] United Kingdom ............... 22913/78

[51] Int. Cl.$^3$ .......................................... C07D 499/44
[52] U.S. Cl. ................................... 424/246; 544/25; 544/21
[58] Field of Search .......................... 544/25, 27, 21; 424/246

[56] References Cited

U.S. PATENT DOCUMENTS

| | | | |
|---|---|---|---|
| 3,971,778 | 7/1976 | Cook et al. | 260/243 C |
| 4,017,515 | 4/1977 | Cook et al. | 260/332.3 R |
| 4,024,133 | 5/1977 | Cook et al. | 260/243 C |
| 4,024,137 | 5/1977 | Cook et al. | 260/243 C |
| 4,032,950 | 7/1977 | Cook et al. | 260/243 C |
| 4,060,686 | 11/1977 | Bradshaw et al. | 544/22 |
| 4,064,346 | 12/1977 | Cook et al. | 544/30 |
| 4,079,178 | 3/1978 | Cook et al. | 544/25 |
| 4,091,209 | 5/1978 | Cook et al. | 544/16 |
| 4,092,477 | 3/1978 | Cook et al. | 544/26 |
| 4,093,803 | 6/1978 | Cook et al. | 544/27 |
| 4,095,021 | 6/1978 | Bradshaw et al. | 544/22 |
| 4,098,888 | 7/1978 | Ochiai et al. | 424/246 |
| 4,103,084 | 7/1978 | Bradshaw et al. | 544/27 |
| 4,144,392 | 3/1979 | Bradshaw et al. | 544/27 |
| 4,144,393 | 3/1979 | Bradshaw et al. | 544/28 |
| 4,152,432 | 5/1979 | Heymes | 424/246 |
| 4,162,360 | 7/1979 | Bradshaw et al. | 544/16 |
| 4,165,430 | 8/1979 | Bradshaw et al. | 544/22 |
| 4,166,115 | 8/1979 | Takaya et al. | 424/246 |

FOREIGN PATENT DOCUMENTS

| | | |
|---|---|---|
| 866422 | 10/1970 | Belgium . |
| 772030 | 3/1977 | South Africa . |
| 781502 | 3/1978 | South Africa . |
| 781630 | 3/1978 | South Africa . |
| 781870 | 3/1978 | South Africa . |
| 782168 | 3/1978 | South Africa . |
| 1399086 | 6/1975 | United Kingdom . |
| 1496757 | 1/1978 | United Kingdom . |

OTHER PUBLICATIONS

Tsochiya et al., Antimicrobial Agents & Chemotherapy 14(4), 557–560 (1978).
Numata et al., J. Antibiotics XXXI, (12), 1262–1271 (1978).
C. F. Acad. Sc., 248, 1847 (1977) Heymes et al., English Abstract.
Heymes et al., Tetrahedron 34, 2233–2243, (1978).
Hamilton-Miller et al., Jour. Antimicrobial Chemotherapy, 4, 437–444, (1978).
Hem. Pharm. Bull. 25, (11), 3115–3118, (1977).

Primary Examiner—Nicholas S. Rizzo
Attorney, Agent, or Firm—Bacon & Thomas

[57] ABSTRACT

Cephalosporin antibiotics of the general formula

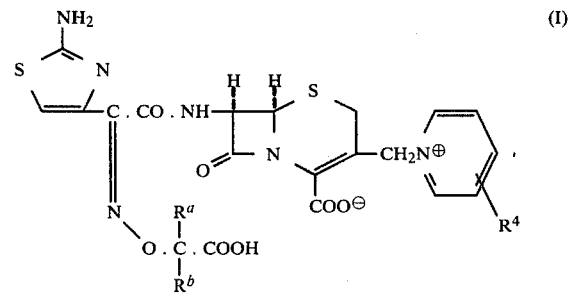

(I)

(wherein $R^a$ and $R^b$, which may be the same or different, each represent a $C_{1-4}$ alkyl group or $R^a$ and $R^b$ together with the carbon atom to which they are attached form a $C_{3-7}$ cycloalkylidene group; and $R^4$ represents hydrogen or a 3- or 4-carbamoyl group) exhibit broad spectrum antibiotic activity, the activity being unusually high against gram-negative organisms such as strains of Pseudomonas organisms. A particular antibiotic compound of formula (I) possessing excellent antibacterial activity against strains of Pseudomonas organisms, as well as other valuable therapeutic properties, is (6R,7R)-7-[(Z)-2-(2-aminothiazol-4-yl)-2-(2-carboxyprop-2-oxyimono) acetamido]-3-(1-pyridiniummethyl)-ceph-3-em-4 carboxylate. The invention also includes the non-toxic salts and non-toxic metabolically labile esters of compounds of formula (I). Also described are compositions containing the antibiotics of the invention and processes for the preparation of such antibiotics.

6 Claims, No Drawings

(6R,7R)-7-[(Z)-2-(2-AMINOTHIAZOL-4-YL)-2-(2-CARBOXYPROP-2-OXYIMINO)ACETAMIDO]-3-(1-PYRIDINIUMMETHYL)-CEPH-3-EM-4-CARBOXYLATE AND SALTS THEREOF

This invention is concerned with cephalosporin compounds possessing valuable antibiotic properties.

The cephalosporin compounds in this specification are named with reference to "cepham" after *J.Amer.-Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram-positive and gram-negative microorganisms, and a significant amount of research has been directed to the development of various types of broad spectrum cephalosporin antibiotics.

Thus, for example, in our British Pat. No. 1,399,086, we describe a novel class of cephalosporin antibiotics containing a 7β-(α-etherified oximino)-acylamido group, the oximino group having the syn configuration. This class of antibiotic compounds is characterised by high antibacterial activity against a range of gram-positive and gram-negative organisms coupled with particularly high stability to β-lactamases produced by various gram-negative organisms.

The discovery of this class of compounds has stimulated further research in the same area in attempts to find compounds which have improved properties, for example against particular classes of organisms especially gram-negative organisms.

In our British Pat. No. 1,496,757, we describe cephalosporin antibiotics containing a 7β-acylamido group of the formula

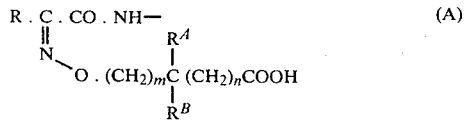

(wherein R is a thienyl or furyl group; $R^A$ and $R^B$ may vary widely and may, for example, be $C_{1-4}$ alkyl groups or together with the carbon atom to which they are attached form a $C_{3-7}$ cycloalkylidene group, and m and n are each 0 or 1 such that the sum of m and n is 0 or 1), the compounds being syn isomers or mixtures of syn and anti isomers containing at least 90% of the syn isomer. The 3-position of the cephalosporin molecule may be unsubstituted or may contain one of a wide variety of possible substituents. These compounds have been found to have particularly good activity against gram-negative organisms.

Furthermore, in our British Pat. No. 1,522,140 we describe cephalosporin antibiotics of the formula

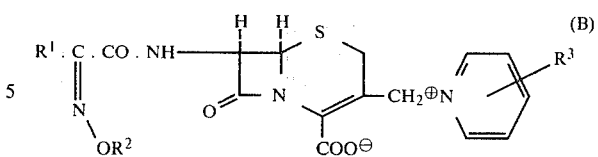

(wherein $R^1$ represents a furyl or thienyl group; $R^2$ represents a $C_1$–$C_4$ alkyl group, a $C_3$–$C_7$ cycloalkyl group, a furylmethyl or thienylmethyl group; and $R^3$ represents a hydrogen atom or a carbamoyl, carboxy, carboxymethyl, sulpho or methyl group), the compounds being syn isomers or existing as mixtures of syn and anti isomers containing at least 90% of the syn isomer. These compounds exhibit high antibacterial activity against a broad range of gram-positive and gram-negative organisms. The compounds also possess high stability to β-lactamases produced by various gram-negative organisms, as well as good stability in vivo.

Other compounds of similar structure have been developed from these compounds in further attempts to find antibiotics having improved broad spectrum antibiotic activity and/or high activity against gram-negative organisms. Such developments have involved variations in not only the 7β-acylamido groups in the above formulae but also the introduction of particular groups in the 3-position of the cephalosporin molecule. Thus, for example, in Belgian Pat. No. 852,427, there are described cephalosporin antibiotic compounds falling within the general scope of our British Pat. No. 1,399,086, and wherein the group R in formula (A) above may be replaced by a variety of different organic groups, including 2-aminothiazol-4-yl, and the oxygen atom in the oxyimino group is attached to an aliphatic hydrocarbon group which may itself be substituted by, for example, carboxy. In such compounds, the substituent at the 3-position is an acyloxymethyl, hydroxymethyl, formyl or optionally substituted heterocyclic-thiomethyl group.

Furthermore, Belgian Pat. No. 836,813 described cephalosporin compounds wherein the group R in formula (A) above may be replaced by, for example, 2-aminothiazol-4-yl, and the oxyimino group is a hydroxyimino or blocked hydroxyimino group, e.g. a methoxyimino group. In such compounds, the 3-position of the cephalosporin molecule is substituted by a methyl group which may itself be optionally substituted by any of a large number of residues of nucleophilic compounds therein described, e.g. the pyridinium group which may be substituted, for example by a carbamoyl group. In the above-mentioned Specification no antibiotic activity is ascribed to such compounds which are only mentioned as intermediates for the preparation of antibiotics described in that Specification.

Belgian Pat. No. 853,545 describes cephalosporin antibiotics wherein the 7β-acylamido side chain is primarily a 2-(2-aminothiazol-4-yl)-2-(syn)-methoxyiminoacetamido group and the substituent in the 3-position is broadly defined in a similar manner to that in the above-mentioned Belgian Pat. No. 836,813. Compounds specifically exemplified in the Specification include compounds in which the 3-position is substituted by a pyridiniummethyl or 4-carbamoylpyridiniummethyl group.

We have now discovered that by an appropriate selection of a small number of particular groups at the 7β-position in combination with either a pyridiniummethyl or a 3- or 4-carbamoylpyridiniummethyl group at the 3-position, cephalosporin compounds having particularly advantageous activity (described in more detail below) against a wide range of commonly encountered pathogenic organisms may be obtained.

The present invention provides cephalosporin antibiotics of the general formula:

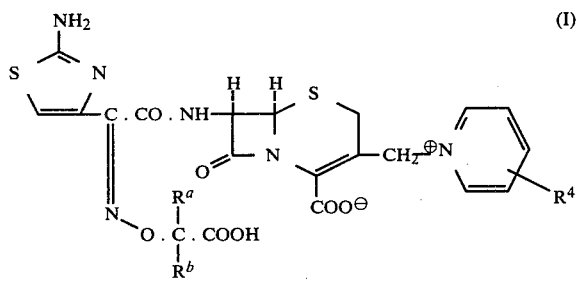

(wherein $R^a$ and $R^b$, which may be the same or different, each represent a $C_{1-4}$ alkyl group (preferably a straight chain alkyl group, i.e. a methyl, ethyl, n-propyl or n-butyl group and particularly a methyl or ethyl group) or $R^a$ and $R^b$ together with the carbon atom to which they are attached form a $C_{3-7}$ cycloalkylidene group, preferably a $C_{3-5}$ cycloalkylidene group; and $R^4$ represents hydrogen or a 3- or 4-carbamoyl group) and non-toxic salts and non-toxic metabolically labile esters thereof.

The compounds according to the invention are syn isomers. The syn isomeric form is defined by the configuration of the group

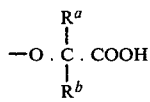

with respect to the carboxamido group. In this Specification the syn configuration is denoted structurally as

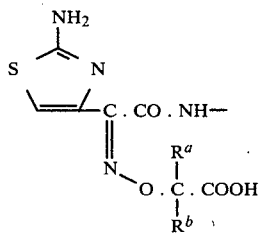

It will be understood that since the compounds according to the invention are geometric isomers, some admixture with the corresponding anti isomer may occur.

The invention also includes within its scope the solvates (especially the hydrates) of the compounds of formula (I). It also includes within its scope salts of esters of compounds of formula (I).

The compounds according to the present invention may exist in tautomeric forms (for example in respect of the 2-aminothiazolyl group) and it will be understood that such tautomeric forms, e.g. the 2-iminothiazolinyl form, are included within the scope of the invention.

Moreover, the compounds of formula (I) depicted above may also exist in alternative zwitterionic forms, for example wherein the 4-carboxyl group is protonated and the carboxyl group in the 7-side chain is deprotonated, which alternative forms are included within the scope of the present invention.

It will also be appreciated that when $R^a$ and $R^b$ in the above formula represent different $C_{1-4}$ alkyl groups, the carbon atom to which they are attached will comprise a centre of asymmetry. Such compounds are diastereoisomeric and the present invention embraces individual diastereoisomers of these compounds as well as mixtures thereof.

The compounds according to the invention exhibit broad spectrum antibiotic activity. Against gram-negative organisms the activity is unusually high. This high activity extends to many β-lactamase-producing gram-negative strains. The compounds also possess high stability to β-lactamases produced by a range of gram-negative organisms.

Compounds according to the invention have been found to exhibit unusually high activity against strains of Pseudomonas organisms, e.g. strains of *Pseudomonas aeruginosa* as well as high activity against various members of the Enterobacteriaceae (e.g. strains of *Escherichia coli, Klebsiella pneumoniae, Salmonella typhimurium, Shigella sonnei, Enterobacter cloacae, Serratia marcescens,* Providence species, *Proteus mirabilis,* and especially indole-positive Proteus organisms such as *Proteus vulgaris* and *Proteus morganii*) and strains of *Haemophilus influenzae*.

The antibiotic properties of the compounds according to the invention compare very favourably with those of the aminoglycosides such as amikacin or gentamicin. In particular, this applies to their activity against strains of various Pseudomonas organisms which are not susceptible to the majority of existing commercially available antibiotic compounds. Unlike the aminoglycosides, cephalosporin antibiotics normally exhibit low toxicity in man. The use of aminoglycosides in human therapy tends to be limited or complicated by the high toxicity of these antibiotics. The cephalosporin antibiotics of the present invention thus possess potentially great advantages over the aminoglycosides.

Non-toxic salt derivatives which may be formed by reaction of either or both of the carboxyl groups present in the compounds of general formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenylethylbenzylamine, dibenzylethylenediamine, ethanolamine, diethanolamine and N-methylglucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quaternary amino groups or sulphonic acid groups, or with a resin containing carboxyl groups, e.g. a polyacrylic acid resin. Soluble base salts (e.g. alkali metal salts such as the sodium salt) of compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

These and other salt derivatives such as the salts with toluene-p-sulphonic and methanesulphonic acids may be employed as intermediates in the preparation and/or purification of the present compounds of formula (I), for example in the processes described below.

Non-toxic metabolically labile ester derivatives which may be formed by esterification of either or both carboxyl groups in the parent compound of formula (I) include acyloxyalkyl esters e.g. lower alkanoyloxymethyl or -ethyl esters such as acetoxy-methyl or -ethyl or pivaloyloxymethyl esters. In addition to the above ester derivatives, the present invention includes within its scope compounds of formula (I) in the form of other physiologically acceptable equivalents, i.e. physiologically acceptable compounds which, like the metabolically labile esters, are converted in vivo into the parent antibiotic compound of formula (I).

A preferred group of compounds according to the invention by virtue of their high antibiotic activity are those compounds of formula (I) above wherein $R^4$ represents hydrogen, i.e. compounds of the general formula:

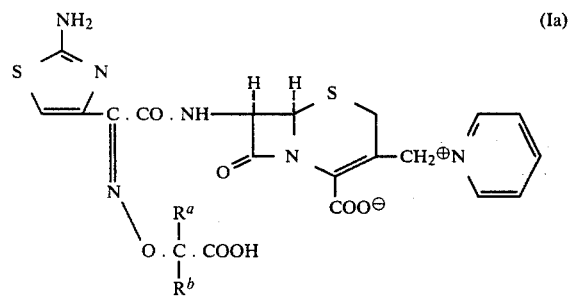

wherein $R^a$ and $R^b$ have the above defined meanings, and their non-toxic salts and non-toxic metabolically labile esters.

An outstanding compound of formula (Ia) is (6R,7R)-7-[(Z)-2-(2-aminothiazol-4-yl)-2-(2-carboxyprop-2-oxyimino)acetamido]-3-(1-pyridiniummethyl)-ceph-3-em-4-carboxylate which has the formula:

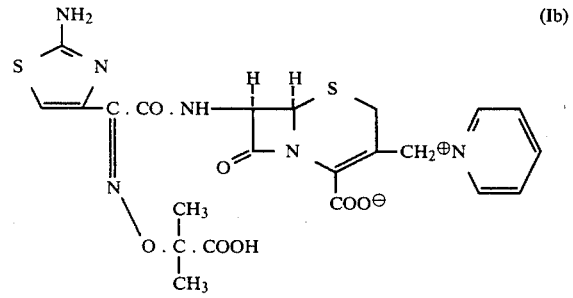

together with its non-toxic salts (e.g. sodium salt) and non-toxic metabolically labile esters. The compound of formula (Ib) possesses to an outstanding extent the general antibiotic properties set out above for the compounds of general formula (I). However one may emphasise its excellent activity against strains of Pseudomonas organisms. The compound has excellent antibacterial properties which are not impaired by human serum, and, moreover, the effect of increased inocula against the compound is low. The compound is rapidly bactericidal at concentrations close to the minimum inhibitory concentration. It is well distributed in the bodies of small rodents giving useful therapeutic levels after subcutaneous injection. In primates the compound gives high and long lasting serum levels after intramuscular injection. The serum half-life in primates points to the probability of comparatively long half-life in man, with the possibility of less frequent dosages being required for less serious infections. Experimental infections in mice with gram-negative bacteria were successfully treated using the compound and, in particular, excellent protection was obtained against strains of Pseudomonas aeruginosa, an organism normally not susceptible to treatment with cephalosporin antibiotics. This protection was comparable with the treatment with an aminoglycoside such as amikacin. Acute toxicity tests with the compound in mice gave $LD_{50}$ values in excess of 1.0 g/kg. No nephrotoxicity was observed in rats at dosages of 2.0 g/kg.

Another compound possessing not dissimilar properties to the compound of formula (Ib) is (6R,7R)-7-[(Z)-2-(2-aminothiazol-4-yl)-2-(1-carboxycyclobut-1-oxyimino)acetamido]-3-(1-pyridiniummethyl)-ceph-3-em-4-carboxylate, together with its non-toxic salts and non-toxic metabolically labile esters.

Other examples of preferred compounds according to the present invention include the following compounds of formula (I) and their non-toxic salts and non-toxic metabolically labile esters, namely:

(6R,7R)-7-[(Z)-2-(2-aminothiazol-4-yl)-2-(2-carboxyprop-2-oxyimino)acetamido]-3-(4-carbamoyl-1-pyridiniummethyl)-ceph-3-em-4-carboxylate;

(6R,7R)-7-[(Z)-2-(2-aminothiazol-4-yl)-2-(1-carboxycycloprop-1-oxyimino)acetamido]-3-(1-pyridiniummethyl)-ceph-3-em-4-carboxylate;

(6R,7R)-7-[(Z)-2-(2-aminothiazol-4-yl)-2-(1-carboxycyclopent-1-yloxyimino)acetamido]-3-(1-pyridiniummethyl)-ceph-3-em-4-carboxylate; and (6R,7R)-7-[(Z)-2-(2-aminothiazol-4-yl)-2-(1-carboxycyclobut-1-oxyimino)acetamido]-3-(4-carbamoyl-1-pyridiniummethyl)-ceph-3-em-4-carboxylate.

Other compounds according to the present invention include for example those wherein the groups $R^a$, $R^b$ and $R^4$ in formula (I) are as follows:

|   |   | $R^a$ | $R^b$ | $R^4$ |
|---|---|---|---|---|
| a) | Alkyl groups | | | |
|   |   | —CH₃ | —C₂H₅ | H |
|   |   | —C₂H₅ | —C₂H₅ | " |
|   |   | —CH₃ | —CH₃ | 3-CONH₂ |
|   |   | " | —C₂H₅ | " |
|   |   | —C₂H₅ | " | " |
|   |   | —CH₃ | " | 4-CONH₂ |
|   |   | —C₂H₅ | " | " |

$$R^a—C—R^b$$

|   |   | $R^4$ |
|---|---|---|
| b) | Cycloalkylidene groups | |
|   | Cyclobutylidene | 3-CONH₂ |
|   | Cyclopentylidene | 3-CONH₂ |
|   | " | 4-CONH₂ |
|   | Cyclohexylidene | H |
|   | " | 3-CONH₂ |
|   | " | 4-CONH₂ |
|   | Cyclopropylidene | 3-CONH₂ |

| | |
|---|---|
| -continued | |
| " | 4-CONH$_2$ |

The compounds of formula (I) may be used for treating a variety of diseases caused by pathogenic bacteria in human beings and animals, such as respiratory tract infections and urinary tract infections.

According to another embodiment of the invention we provide a process for the preparation of an antibiotic compound of general formula (I) as hereinbefore defined or a non-toxic salt or non-toxic metabolically labile ester thereof which comprises (A) acylating a compound of the formula

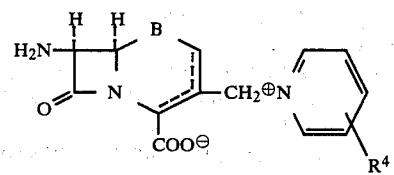 (II)

[wherein $R^4$ is as defined above; B is $>S$ or $>S\to O$ ($\alpha$- or $\beta$-); and the dotted line bridging the 2-, 3-, and 4-positions indicates that the compound is a ceph-2-em or ceph-3-em compound] or a salt, e.g. an acid addition salt (formed with, for example, a mineral acid such as hydrochloric, hydrobromic, sulphuric, nitric or phosphoric acid or an organic acid such as methanesulphonic or toluene-p-sulphonic acid) or an N-silyl derivative thereof, or a corresponding compound having a group of formula —COOR$^5$ at the 4-position [where $R^5$ is a hydrogen atom or a carboxyl blocking group, e.g. the residue of an ester-forming aliphatic or araliphatic alcohol or an ester-forming phenol, silanol or stannanol (the said alcohol, phenol, silanol or stannanol preferably containing 1–20 carbon atoms)] and having an associated anion $A^\ominus$ such as a halide, e.g. chloride or bromide, or trifluoroacetate anion, with an acid of formula

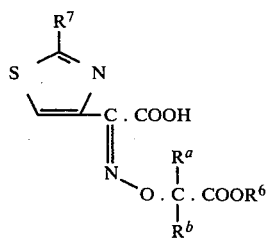 (III)

(wherein $R^a$ and $R^b$ are as hereinbefore defined; $R^6$ represents a carboxyl blocking group, e.g. as described for $R^5$; and $R^7$ is an amino or protected amino group) or with an acylating agent corresponding thereto; or (B) reacting a compound of formula

 (IV)

(wherein $R^a$, $R^b$, $R^7$, B and the dotted line are as hereinbefore defined; $R^8$ and $R^{8a}$ may independently represent hydrogen or a carboxyl blocking group; and X is a replaceable residue of a nucleophile, e.g. an acetoxy or dichloroacetoxy group or a halogen atom such as chlorine, bromine or iodine) or a salt thereof, with a pyridine compound of the formula

 (V)

(wherein $R^4$ is as defined above); whereafter, if necessary and/or desired in each instance, any of the following reactions, in any appropriate sequence, are carried out:

(i) conversion of a $\Delta^2$-isomer into the desired $\Delta^3$-isomer, (ii) reduction of a compound wherein B is $<S\to O$ to form a compound wherein B is $>S$, (iii) conversion of a carboxyl group into a non-toxic salt or non-toxic metabolically labile ester function, and (iv) removal of any carboxyl blocking and/or N-protecting groups.

In the above-described process (A), the starting material of formula (II) is preferably a compound wherein B is $>S$ and the dotted line represents a ceph-3-em compound. One such starting material which has been found to be particularly suitable for use in process (A) is N-(7-aminoceph-3-em-3-ylmethyl)pyridinium-4'-carboxylate dihydrochloride on account of the high purity in which it can be prepared.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Acylations employing acid halides may be effected in aqueous and non-aqueous reaction media, conveniently at temperatures of from −50° to +50° C., preferably −20° to +30° C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g.

ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N,ethyl-N'-γ-dimethylaminopropylcarbodiimide; a carbonyl compound such as carbonyldiimidazole; or an isoxazolium salt such as N-ethyl-5-phenylisoxazolium perchlorate.

Acylation may also be effected with other amide-forming derivatives of acids of formula (III) such as, for example, an activated ester, a symmetrical anhydride or a mixed anhydride (e.g. formed with pivalic acid or with a haloformate, such as a lower alkylhaloformate). Mixed anhydrides may also be formed with phosphorus acids (for example phosphoric or phosphorous acids), sulphuric acid or aliphatic or aromatic sulphonic acids (for example toluene-p-sulphonic acid). An activated ester may conveniently be formed in situ using, for example, 1-hydroxybenzotriazole in the presence of a condensing agent as set out above. Alternatively, the activated ester may be preformed.

Acylation reactions involving the free acids or their above-mentioned amide-forming derivatives are desirably effected in an anhydrous reaction medium, e.g. methylene chloride, tetrahydrofuran, dimethylformamide or acetonitrile.

If desired, the above acylation reactions may be carried out in the presence of a catalyst such as 4-dimethylaminopyridine.

The acids of formula (III) and acylating agents corresponding thereto may, if desired, be prepared and employed in the form of their acid addition salts. Thus, for example, acid chlorides may conveniently be employed as their hydrochloride salts, and acid bromides as their hydrobromide salts.

The pyridine compound of formula (V) may act as a nucleophile to displace a wide variety of substituents X from the cephalosporin of formula (IV). To some extent the facility of the displacement is related to the $pK_a$ of the acid HX from which the substituent is derived. Thus atoms or groups X derived from strong acids tend, in general, to be more easily displaced than atoms or groups derived from weaker acids. The facility of the displacement is also related, to some extent, to the precise character of the substituent $R^4$ in the compound of formula (V).

The displacement of X by the pyridine compound of formula (V) may conveniently be effected by maintaining the reactants in solution or suspension. The reaction is advantageously effected using from 1 to 10 moles of the pyridine compound.

Nucleophilic displacement reactions may conveniently be carried out on those compounds of formula (IV) wherein the substituent X is a halogen atom or an acyloxy group for example as discussed below.

Acyloxy groups

Compounds of formula (IV) wherein X is an acetoxy group are convenient starting materials for use in the nucleophilic displacement reaction with the pyridine compound of formula (V). Alternative starting materials in this class include compounds of formula (IV) in which X is the residue of a substituted acetic acid e.g. chloroacetic acid, dichloroacetic acid and trifluoroacetic acid.

Displacement reactions on compounds (IV) possessing X substituents of this class, particularly in the case where X is an acetoxy group, may be facilitated by the presence in the reaction medium of iodide or thiocyanate ions. Reactions of this type are described in more detail in British Pat. Nos. 1,132,621 and 1,171,603.

The substituent X may also be derived from formic acid, a haloformic acid such as chloroformic acid, or a carbamic acid.

When using a compound of formula (IV) in which X represents an acetoxy or substituted acetoxy group, it is generally desirable that the group $R^8$ in formula (IV) should be a hydrogen atom and that B should represent $>S$. In this case, the reaction is advantageously effected in an aqueous medium, preferably at a pH of 5 to 8, particularly 5.5 to 7.

The above-described process employing compounds of formula (IV) in which X is the residue of a substituted acetic acid may be carried out as described in British Pat. No. 1,241,657.

When using compounds of formula (IV) in which X is an acetoxy group, the reaction is conveniently effected at a temperature of 30° to 110° C., preferably 50° to 80° C.

Halogens

Compounds of formula (IV) in which X is a chlorine, bromine or iodine atom can also be conveniently used as starting materials in the nucleophilic displacement reaction with the pyridine compound of formula (V). When using compounds of formula (IV) in this class, B may represent $>S\rightarrow O$ and $R^8$ may represent a carboxyl blocking group. The reaction is conveniently effected in a non-aqueous medium which preferably comprises one or more organic solvents, advantageously of a polar nature, such as ethers, e.g. dioxan or tetrahydrofuran, esters, e.g. ethyl acetate, amides, e.g. formamide and N,N-dimethylformamide, and ketones e.g. acetone. In certain cases the pyridine compound itself may be the solvent. Other suitable organic solvents are described in more detail in British Pat. No. 1,326,531. The reaction medium should be neither extremely acidic nor extremely basic. In the case of reactions carried out on compounds of formula (IV) in which $R^8$ and $R^{8a}$ are carboxyl blocking groups the 3-pyridiniummethyl product will be formed as the corresponding halide salt which may, if desired, be subjected to one or more ion exchange reactions to obtain a salt having the desired anion.

When using compounds of formula (IV) in which X is a halogen atom as described above, the reaction is conveniently effected at a temperature of $-10°$ to $+50°$ C., preferably $+10°$ to $+30°$ C.

The reaction product may be separated from the reaction mixture, which may contain, for example, unchanged cephalosporin starting material and other substances, by a variety of processes including recrystallisation, ionophoresis, column chromatography and use of ion-exchangers (for example by chromatography on ion-exchange resins) or macroreticular resins.

$\Delta^2$-Cephalosporin ester derivatives obtained in accordance with the process of the invention may be converted into the corresponding $\Delta^3$-derivative by, for example, treatment of the $\Delta^2$-ester with a base such as pyridine or triethylamine.

A ceph-2-em reaction product may also be oxidised to yield the corresponding ceph-3-em 1-oxide, for example by reaction with a peracid, e.g. peracetic or m- chloroperbenzoic acid; the resulting sulphoxide may, if desired, subsequently be reduced as described hereinafter to yield the corresponding ceph-3-em sulphide.

Where a compound is obtained in which B is $>S\rightarrow O$ this may be converted to the corresponding sulphide by, for example, reduction of the corresponding acyloxysulphonium or alkoxysulphonium salt prepared in situ by reaction with e.g. acetyl chloride in the case of an acetoxysulphonium salt, reduction being effected by, for example, sodium dithionite or by iodide ion as in a solution of potassium iodide in a water-miscible solvent e.g. acetic acid, acetone, tetrahydrofuran, dioxan, dimethylformamide or dimethylacetamide. The reaction may be effected at a temperature of from $-20°$ to $+50°$ C.

Metabolically labile ester derivatives of the compounds of formula (I) may be prepared by reacting a compound of formula (I) or a salt or protected derivative thereof with an appropriate esterifying agent such as an acyloxyalkyl halide (e.g. iodide) conveniently in an inert organic solvent such as dimethylformamide or acetone, followed, where necessary, by removal of any protecting groups.

Base salts of the compounds of formula (I) may be formed by reacting an acid of formula (I) with the appropriate base. Thus, for example, sodium or potassium salts may be prepared using the respective 2-ethylhexanoate or hydrogen carbonate salt. Acid addition salts may be prepared by reacting a compound of formula (I) or a metabolically labile ester derivative thereof with the appropriate acid.

Where a compound of formula (I) is obtained as a mixture of isomers, the syn isomer may be obtained by, for example, conventional methods such as crystallisation or chromatography.

For use as starting materials for the preparation of compounds of general formula (I) according to the invention, compounds of general formula (III) and acid halides and anhydrides corresponding thereto in their syn isomeric form or in the form of mixtures of the syn isomers and the corresponding anti isomers containing at least 90% of the syn isomer are preferably used.

Acids of formula (III) (provided that $R^a$ and $R^b$ together with the carbon atom to which they are attached do not form a cyclopropylidene group) may be prepared by etherification of a compound of formula

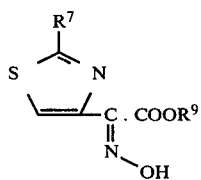
(VI)

(wherein $R^7$ is as hereinbefore defined and $R^9$ represents a carboxyl blocking group), by reaction with a compound of general formula

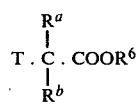
(VII)

(wherein $R^a$ and $R^b$ and $R^6$ are as hereinbefore defined and T is halogen such as chloro, bromo or iodo; sulphate; or sulphonate such as tosylate), followed by removal of the carboxyl blocking group $R^9$. Separation of isomers may be effected either before or after such etherification. The etherification reaction is generally carried out in the presence of a base, e.g. potassium carbonate or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oxyimino group is substantially unchanged by the etherification reaction. The reaction should be effected in the presence of a base if an acid addition salt of a compound of formula (VI) is used. The base should be used in sufficient quantity to neutralise rapidly the acid in question.

Acids of general formula (III) may also be prepared by reaction of a compound of formula

(VIII)

wherein $R^7$ and $R^9$ are as hereinbefore defined) with a compound of formula

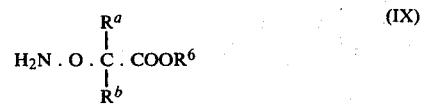
(IX)

(wherein $R^a$, $R^b$ and $R^6$ are as defined above), followed by removal of the carboxyl blocking group $R^9$, and where necessary by the separation of syn and anti isomers.

The last-mentioned reaction is particularly applicable to the preparation of acids of formula (III) wherein $R^a$ and $R^b$ together with the carbon atom to which they are attached form a cyclopropylidene group. In this case, the relevant compounds of formula (IX) may be prepared in conventional manner, e.g. by means of the synthesis described in Belgian Pat. No. 866,422 for the preparation of t-butyl 1-aminooxycyclopropane carboxylate.

The acids of formula (III) may be converted to the corresponding acid halides and anhydrides and acid addition salts by conventional methods, for example as described hereinabove.

Where X is a halogen (i.e. chlorine, bromine or iodine) atom in formula (IV), ceph-3-em starting compounds may be prepared in conventional manner, e.g. by halogenation of a 7β-protected amino-3-methylceph-3-em-4-carboxylic acid ester 1β-oxide, removal of the 7β-protecting group, acylation of the resulting 7β-amino compound to form the desired 7β-acylamido group, e.g. in an analogous manner to process (A) above, followed by reduction of the 1β-oxide group later in the sequence. This is described in British Pat. No. 1,326,531. The corresponding ceph-2-em compounds may be prepared by the method of Dutch published Patent Application No. 6,902,013 by reaction of a 3-methylceph-2-em compound with N-bromosuccinimide to yield the corresponding 3-bromomethylceph-2-em-compound.

Where X in formula (IV) is an acetoxy group, such starting materials may be prepared for example by acylation of 7-aminocephalosporanic acid, e.g. in an analogous manner to process (A) above. Compounds of formula (IV) in which X represents other acyloxy groups can be prepared by acylation of the corresponding 3-hydroxymethyl compounds which may be prepared for example by hydrolysis of the appropriate 3-acetoxymethyl compounds, e.g. as described in British Pat. Nos. 1,474,519 and 1,531,212.

The starting materials of formula (II) may also be prepared in conventional manner, for example, by nucleophilic displacement of the corresponding 3-acetoxymethyl compound with the appropriate nucleophile, e.g. as described in British Pat. No. 1,028,563.

A further method for the preparation of the starting materials of formula (II) comprises deprotecting a corresponding protected 7β-amino compound in conventional manner e.g. using $PCl_5$.

It should be appreciated that in some of the above transformations it may be necessary to protect any sensitive groups in the molecule of the compound in question to avoid undesirable side reactions. For example, during any of the reaction sequences referred to above it may be necessary to protect the $NH_2$ group of the aminothiazolyl moiety, for example by tritylation, acylation (e.g. chloroacetylation), protonation or other conventional method. The protecting group may thereafter be removed in any convenient way which does not cause breakdown of the desired compound, e.g. in the case of a trityl group by using an optionally halogenated carboxylic acid, e.g. acetic acid, formic acid, chloroacetic acid or trifluoroacetic acid or using a mineral acid, e.g. hydrochloric acid or mixtures of such acids, preferably in the presence of a protic solvent such as water or, in the case of a chloroacetyl group, by treatment with thiourea.

Carboxyl blocking groups used in the preparation of compounds of formula (I) or in the preparation of necessary starting materials are desirably groups which may readily be split off at a suitable stage in the reaction sequence, conveniently at the last stage. It may, however, be convenient in some instances to employ non-toxic metabolically labile carboxyl blocking groups such as acyloxy-methyl or -ethyl groups (e.g. acetoxymethyl or -ethyl or pivaloyloxymethyl) and retain these in the final product to give an appropriate ester derivative of a compound of formula (I).

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. Carboxyl blocking group(s) may subsequently be removed by any of the appropriate methods disclosed in the literature; thus, for example, acid or base catalysed hydrolysis is applicable in many cases, as are enzymically-catalysed hydrolyses.

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers, if necessary with an added preservative. The compositions may also take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

If desired, such powder formulations may contain an appropriate non-toxic base in order to improve the water-solubity of the active ingredient and/or to ensure that when the powder is reconstituted with water, the pH of the resulting aqueous formulation is physiologically acceptable. Alternatively, the base may be present in the water with which the powder is reconstituted. The base may be, for example, an inorganic base such as sodium carbonate, sodium bicarbonate or sodium acetate, or an organic base such as lysine or lysine acetate.

The antibiotic compounds may also be formulated as suppositories, e.g. containing conventional suppository bases such as cocoa butter or other glycerides.

Compositions for veterinary medicine may, for example, be formulated as intramammary preparations in either long acting or quick-release bases.

The compositions may contain from 0.1% upwards, e.g. 0.1–99%, of the active material, depending on the method of administration. When the compositions comprise dosage units, each unit will preferably contain 50–1500 mg of the active ingredient. The dosage as employed for adult human treatment will preferably range from 500 to 6000 mg per day, depending on the route and frequency of administration. For example, in adult human treatment 1000 to 3000 mg per day administered intravenously or intramuscularly will normally suffice. In treating Pseudomonas infections higher daily doses may be required.

The antibiotic compounds according to the invention may be administered in combination with other therapeutic agents such as antibiotics, for example penicillins or other cephalosporins.

The following Examples illustrate the invention. All temperatures are in °C. 'Petrol' means petroleum ether (b.p. 40°–60°).

Proton magnetic resonance (p.m.r.) spectra were determined at 100 MHz. The integrals are in agreement with the assignments, coupling constants, J, are in Hz, the signs not being determined; s=singlet, d=doublet, dd=double doublet, M=multiplet and ABq=AB quartet.

PREPARATION 1

Ethyl (Z)-2-(2-aminothiazol-4-yl)-2-(hydroxyimino)acetate

To a stirred and ice-cooled solution of ethyl acetoacetate (292 g) in glacial acetic acid (296 ml) was added a solution of sodium nitrite (180 g) in water (400 ml) at such a rate that the reaction temperature was maintained below 10° C. Stirring and cooling were continued for about 30 min., when a solution of potassium chloride (160 g) in water (800 ml) was added. The resulting mixture was stirred for one hour. The lower oily phase was separated and the aqueous phase was extracted with diethyl ether. The extract was combined with the oil, washed successively with water and saturated brine, dried, and evaporated. The residual oil, which solidified on standing, was washed with petrol and dried in vacuo over potassium hydroxide, giving ethyl (Z)-2-(hydroxyimino)-3-oxobutyrate (309 g).

A stirred and ice-cooled solution of ethyl (Z)-2-(hydroxyimino)-3-oxobutyrate (150 g) in dichloromethane (400 ml) was treated dropwise with sulphuryl chloride (140 g). The resulting solution was kept at room temperature for 3 days, then evaporated. The residue was dissolved in diethyl ether, washed with water until the washings, were almost neutral, dried, and evaporated. The residual oil (177 g) was dissolved in ethanol (500 ml) and dimethylaniline (77 ml) and thiourea (42 g) were added with stirring. After two hours, the product was collected by filtration, washed with ethanol and dried to give the title compound (73 g); m.p. 188° (decomp.).

PREPARATION 2

Ethyl (Z)-2-hydroxyimino-2-(2-tritylaminothiazol-4-yl)acetate, hydrochloride, Trityl chloride (16.75 g) was added portionwise over 2 hours to a stirred and cooled (−30°) solution of the product of Preparation 1 (12.91 g) in dimethylformamide (28 ml) containing triethylamine (8.4 ml). The mixture was allowed to warm to 15° over one hour, stirred for a further 2 hours and then partitioned between water (500 ml) and ethyl acetate (500 ml). The organic phase was separated, washed with water (2×500 ml) and then shaken with 1 N HCl (500 ml). The precipitate was collected, washed successively with water (100 ml), ethyl acetate (200 ml) and ether (200 ml) and dried in vacuo to provide the title compound as a white solid (16.4 g); m.p. 184° to 186° (decomp).

PREPARATION 3

Ethyl (Z)-2-(2-t-butoxycarbonylprop-2-oxyimino)-2-(2-tritylaminothiazol-4-yl)acetate Potassium carbonate (34.6 g) and t-butyl 2-bromo-2-methylpropionate (24.5 g) in dimethylsulphoxide (25 ml) were added to a stirred solution under nitrogen of the product of Preparation 2 (49.4 g) in dimethylsulphoxide (200 ml) and the mixture was stirred at room temperature for 6 hours. The mixture was poured into water (2 l), stirred for 10 mins., and filtered. The solid was washed with water and dissolved in ethyl acetate (600 ml). The solution was washed successively with water, 2 N hydrochloric acid, water, and saturated brine, dried, and evaporated. The residue was recrystallised from petroleum ether (b.p. 60°–80°) to give the title compound (34 g), m.p. 123.5° to 125°

PREPARATION 4

(Z)-2-(2-t-Butoxycarbonylprop-2-oxyimino)-2-(2-tritylaminothiazol-4-yl)acetic acid The product of Preparation 3 (2 g) was dissolved in methanol (20 ml) and 2 N sodium hydroxide (3.3 ml) was added. The mixture was refluxed for 1.5 hours and then concentrated. The residue was taken up in a mixture of water (50 ml), 2 N hydrochloric acid (7 ml), and ethyl acetate (50 ml). The organic phase was separated, and the aqueous phase extracted with ethyl acetate. The organic solutions were combined, washed successively with water and saturated brine, dried, and evaporated. The residue was recrystallised from a mixture of carbon tetrachloride and petrol to give the title compound (1 g), m.p. 152° to 156° (decomp).

PREPARATION 5

Ethyl (Z)-2-(2-tritylaminothiazol-4-yl)-2-(1-t-butoxycarbonylcyclobut-1-oxyimino) acetate.

The product of Preparation 2 (55.8 g) was stirred under nitrogen in dimethylsulphoxide (400 ml) with potassium carbonate (finely ground, 31.2 g) at room temperature. After 30 minutes, t-butyl 1-bromocyclobutane carboxylate (29.2 g) was added. After 8 hours further potassium carbonate (31.2 g) was added. More potassium carbonate (6×16 g portions) was added during the next three days and further t-butyl 1-bromocyclobutane carboxylate (3.45 g) was added after 3 days. After 4 days in all, the mixture was poured into ice-water (ca. 3 liters) and the solid was collected by filtration and washed well with water and petrol. The solid was dissolved in ethyl acetate and the solution washed with brine (twice), dried with magnesium sulphate and evaporated to a foam. This foam was dissolved in ethyl acetate-petrol (1:2) and filtered through silica gel (500 g). Evaporation gave the title compound (60 g) as a foam, $\nu_{max}$ (CHBr$_3$) 3400 (NH) and 1730 cm$^{-1}$ (ester).

PREPARATION 6

(Z)-2-(1-t-Butoxycarbonylcyclobut-1-oxyimino)-2-(2-tritylaminothiazol-4-yl) acetic acid.

A mixture of the product of Preparation 5 (3.2 g) and potassium carbonate (1.65 g) was refluxed in methanol (180 ml) and water (20 ml) for 9 hours and the mixture was cooled to room temperature. The mixture was concentrated and the residue partitioned between ethyl acetate and water, to which was added 2 N HCl (12.2 ml). The organic phase was separated and the aqueous phase extracted with ethyl acetate. The combined organic extracts were washed with saturated brine, dried and evaporated to give the title compound (2.3 g); $\lambda_{max}$ (ethanol) 265 nm (E$_{1\ cm}$1% 243).

PREPARATION 7

(Z)-2-(1-t-Butoxycarbonylcycloprop-1-oxyimino)-2-(2-tritylaminothiazol-4-yl)acetic acid.

A solution of hydrazine hydrate (0.20 g) in methanol (0.4 ml) was added to a solution of 1-t-butoxycarbonylcycloprop-1-oxyphthalimide (0.61 g; prepared as described in Belgian Pat. No. 866,422) in dichloromethane (7 ml). The mixture was stirred at room temperature for 1 hour, and treated with 5 N aqueous ammonia solution (7 ml). The organic phase was separated and the aqueous phase was extracted with dichloromethane. The combined organic solutions were washed with water, dried, and evaporated. The oily residue (0.30 g) was dissolved in a mixture of ether (5 ml) and ethyl acetate (5 ml). 2-Tritylaminothiazol-4-ylglyoxylic acid (0.73 g; prepared as described in Belgian Pat. No. 864,828) was added. The mixture was stirred at room temperature overnight and then filtered. The solid was washed with a little ether and dried in vacuo to give the title compound (0.5 g), m.p. 156.8°–157.2°; $\nu_{max}$ (CHBr$_3$) 2300–3500 (O—H, N—H); 1750 (t-butyl ester); 1690 cm$^{-1}$ (acid).

PREPARATION 8

Ethyl (Z)-2-(1-t-butoxycarbonylcyclopent-1-yloxyimino)-2-(2-tritylaminothiazol-4-yl)acetate The product of Preparation 2 (10 g) was stirred with t-butyl 2-bromo-cyclopentanecarboxylate (7 g) in dimethylsulphoxide (40 ml) containing potassium carbonate (10 g) under nitrogen at 21° for 21 hours. The mixture was poured into ice-water (500 ml) and the grey solid was collected by filration, washed with water and air dried.

Recrystallisation of this solid from methanol (500 ml) gave the title compound (11.7 g), m.p. 179°–180°, $\nu_{max}$ (CHBr$_3$) 3410 (NH), 1735 (ester), 1275 (ester) and 755 cm$^{-1}$ (phenyl).

PREPARATION 9

(Z)-2-(1-t-Butoxycarbonylcyclopent-1-yloxyimino)-2-(2-tritylaminothiazol-4-yl)acetic acid The product of Preparation 8 (625 mg) was refluxed with 2 N sodium hydroxide solution (0.5 ml) and water (1 ml) in methanol (12 ml) for seven hours. The mixture was left to cool overnight. After dilution with water, orthophosphoric acid was added to adjust the solution to pH 2. The precipitate was extracted with ether and the combined extracts were washed with brine. After drying with magnesium sulphate, the solvent was evaporated to give a gum (493 mg). Recrystallisation from di-isopropyl ether gave the title compound (356 mg) m.p. 171°–173°, $\nu_{max}$(CHBr$_3$) 2500–3500 (OH and NH), 1755 (ester), 1692 (acid) and 755 and 770 cm$^{-1}$ (phenyl).

PREPARATION 10

(6R,7R)-7-amino-3-(1-pyridiniummethyl)ceph-3-em-4-carboxylic acid dihydrochloride (a) A stirred suspension of (6R,7R)-7-(2-thienylacetamido)-3-(1-pyridiniummethyl)ceph-3-em-4-carboxylate (4.15 g) in dichloromethane (30 ml) was treated with N,N-dimethylaniline (5.09 ml) and chlorotrimethylsilane (2.52 ml). This mixture was stirred at 30°–35° for one hour and then cooled to −28° and treated with phosphorus pentachloride (4.16 g), stirred at −25° to −30° for another hour and then poured into a stirred cooled (−20°) solution of butane-1,3-diol (8.1 ml) and dichloromethane (20 ml). The solution was allowed to attain 0° temperature over 30 minutes, and the precipitated solid (A) was filtered, washed with dichloromethane and dried in vacuo. It was redissolved in methanol (17.5 ml), stirred and diluted with dichloromethane (87.5 ml) and the precipitated solid filtered off, washed with dichloromethane and dried in vacuo to yield the title compound as a white solid (3.2 g), $\lambda_{max}$ (pH 6 buffer) 258 nm (E$_{1\ cm}$1% 318); $\tau$(D$_2$O) values include 0.95, 1.32 and 1.84 (pyridinium protons), 4.10 to 4.46 (ABq, J 16 Hz, 3-CH$_2$-), 4.56 (d, J 5 Hz 7-H), 4.70 (d, J 5 Hz, 6-H), 6.14 to 6.50 (ABq, J 17 Hz, C$_2$-H).

(b) Solid (A) prepared as in stage (a) above (8 g) was dissolved in 1 N hydrochloric acid (25 ml). Addition of isopropanol (95 ml) precipitated the crystalline title compound as a dihydrate (4.95 g). $\tau$(D$_2$O) values include 1.02, 1.36 and 1.87 (pyridinium protons); 4.2+4.55 (ABq, J=14 Hz, 3-CH$_2$-); 4.62 (d, J=5 Hz, C$_7$-H); 47.4 (d, J=5 Hz, C$_6$-H); 6.19+6.38 (ABq, J=18 Hz, C$_2$-H). Water content by Karl Fischer method: 9.4%.

EXAMPLE 1

(a) t-Butyl (6R,7R)-3-Acetoxymethyl-7-[(Z)-2-(2-t-butoxycarbonylprop-2-oxyimino)-2-(2-tritylaminothiazol-4-yl) acetamido]ceph-3-em-4-carboxylate A stirred solution of the product of Preparation 4 (572 mg) and t-butyl (6R,7R)-3-acetoxymethyl-7-aminoceph-3-em-4-carboxylate (328 mg) in dimethylformamide (10 ml) was cooled to 0°, and 1-hydroxybenzotriazole (150 mg) was added, followed by dicyclohexylcarbodiimide (225 mg). The mixture was warmed to room temperature, stirred for 5 hours, and allowed to stand overnight. The mixture was filtered, and the white solid washed with a little ether. The filtrate and washings were diluted with water (50 ml) and extracted with ethyl acetate. The organic extracts were combined, washed successively with water, 2 N hydrochloric acid, water, sodium bicarbonate solution, and saturated brine, dried and evaporated. The residue was eluted through a silica colum with ether. The product-containing eluate was collected and concentrated to give the title compound (533 mg). A portion was recrystallised from di-isopropyl ether, m.p. 103° to 113° (decomp.); $[\alpha]_D^{20}$+8.5° (c, 1.0, DMSO). cl (b) (6R,7R)-3-Acetoxymethyl-7-[(Z)-2-(2-aminothiazol-4-yl)-2-(2-carboxyprop-2-oxyimino)acetamido]ceph-3-em-4-carboxylic acid Trifluoroacetic acid (18 ml) was added to a solution of the product of Stage (a) (2.4 g) in anisole (18 ml) at 0°. The mixture was stirred at room temperature for 2 hours and concentrated. The residue was dissolved in ethyl acetate and extracted with saturated sodium bicarbonate solution. The pH of the aqueous extracts was adjusted to 6, and the solution washed with ethyl acetate. The aqueous phase was acidified to pH 1.5 under ethyl acetate, saturated with sodium chloride, and extracted with ethyl acetate. The combined organic extracts were washed with saturated brine, dried and evaporated. The residue was dissolved in warm 50% aqueous formic acid (20 ml) and allowed to stand for 2 hours. The mixture was diluted with water (50 ml), and filtered. The filtrate was concentrated. The residue was taken up in water (50 ml), refiltered, and lyophilized to give the title compound (920 mg), $\lambda_{max}$ (pH 6 buffer) 236 nm (E$_{1\ cm}$1% 250), $\lambda_{inf}$255 nm (E$_{1\ cm}$1% 235), 296 nm (E$_{1\ cm}$1% 103); $[\alpha]_D^{20}$+20.0° (c 1.0, DMSO).

(c) (6R,7R)-7-[(Z)-2-(2-Aminothiazol-4-yl)-2-(2-carboxyprop-2-oxyimino)acetamido]-3-(1-pyridiniummethyl)-ceph-3-em-4-carboxylate, mono-sodium salt Pyridine (2 ml) and the product of Stage (b) (1.8 g) were added to a stirred solution of sodium iodide (7.12 g) in water (2.2 ml) at 80°. The solution was stirred at 80° C. for 1 hour, cooled, and diluted to 100 ml with water. The pH of the solution was adjusted to 6.0 with 2 N sodium hydroxide solution, and this solution was concentrated to remove pyridine. The aqueous residue was diluted to 100 ml with water, methyl isobutyl ketone (2 drops) was added, and the solution was acidified to pH 1 with 2 N hydrochloric acid. The mixture was filtered, and the solid was washed with a little water. The filtrate and washings were collected and washed with ethyl acetate, and the pH adjusted to 6.0 with 2 N sodium hydroxide solution. The solution was concentrated to 50 ml and applied to a column of 500 g Amberlite XAD-2 resin, using first water and then 20% aqueous ethanol as eluting solvent. The product-containing fractions were concentrated and lyophilized to give the title compound, (0.56 g), $\lambda_{max}$ (pH 6 buffer) 253.5 nm ($E_{1\ cm}^{1\%}$ 307), $\lambda_{inf}$ 282 nm ($E_{1\ cm}^{1\%}$ 159), 260 nm ($E_{1\ cm}^{1\%}$ 295); $[\alpha]_D^{20} +24.5°$ (c 1.0, DMSO).

EXAMPLE 2

(6R,7R)-7-[(Z)-2-(2-Aminothiazol-4-yl)-2-(2-carboxyprop-2-oxyimino)acetamido]-3-(4-carbamoyl-1-pyridiniummethyl)-ceph-3-em-4-carboxylate, mono-sodium salt.

Isonicotinamide (0.56 g) was added to a stirred solution of the product of Example 1 (b) (0.59 g) in water (0.7 ml) containing sufficient sodium bicarbonate to give a final pH of 6.5. Sodium iodide (2.1 g) was added and the mixture was stirred at 80° C. for one hour; sodium bicarbonate was added at intervals to maintain a pH in the range 5.5–6.5. The product was isolated substantially as described in Example 1 (c) to give the title compound, (0.09 g), $\lambda_{max}$ (pH 6 buffer) 257.5 nm ($E_{1\ cm}^{1\%}$ 276), $\lambda_{inf}$ 291.5 nm ($E_{1\ cm}^{1\%}$ 125); $\tau(D_2O)$ values include 0.92, 1.70 (4H; pyridinium protons); 3.10 (1H, aminothiazole-5-H); 4.34; 4.64 (2H; ABq; 3-CH$_2$-); 8.54 (6H;-CMe$_2$-).

EXAMPLE 3

(a) t-Butyl (6R,7R)-3-Acetoxymethyl-7-[(Z)-2-(1-t-butoxy-carbonylcyclobut-1-oxyimino)-2-(2-tritylaminothiazol-4-yl)acetamido]-ceph-3-em-4-carboxylate A stirred solution of the product of Preparation 6 (24.2 g) and t-butyl (6R,7R)-3-acetoxymethyl-7-aminoceph-3-em-4-carboxylate (13.6 g) in dimethylformamide (300 ml) was cooled to 0°, treated with 1-hydroxybenzotriazole monohydrate (4.5 g), followed by dicyclohexylcarbodiimide (6.4 g) and the product isolated substantially as described in Example 1 (a) to give the title compound (12.8 g), m.p. 113.5° to 116.5° (decomp.); $[\alpha]_D^{20} +15.0°$ (c 1.0, DMSO).

(b)
(6R,7R)-3-Acetoxymethyl-7-[(Z)-2-(2-aminothiazol-4-yl)-2-(1-carboxycylobut-1-oxyimino)acetamido]ceph-3-em-4-carboxylic acid Trifluoroacetic acid (100 ml) was added to a mixture of the product of Stage (a) (12.5 g) and anisole (5 ml) at 0°. The mixture was treated substantially as described in Example 1 (b) to give the title compound (4 g), $\lambda_{max}$ (pH 6 buffer) 246 nm ($E_{1\ cm}^{1\%}$ 264), $\lambda_{inf}$ 295 nm ($E_{1\ cm}^{1\%}$ 118); $[\alpha]_D^{20} +27.3°$ (c 1.0, DMSO).

(c)
(6R,7R)-7-[(Z)-2-(2-Aminothiazol-4-yl)-2-(1-carboxycyclobut-1-oxyimino)acetamido]-3-(1-pyridiniummethyl)-ceph-3-em-4-carboxylate, mono-sodium salt Pyridine (4.1 ml) and the product of Stage (b) (3.75 g) were added to a stirred solution of sodium iodide (14.6 g) in water (4.5 ml) at 80° C. and the product isolated substantially as described in Example 1 (c) to give title compound (1.3 g) $\lambda_{max}$ (pH 6 buffer) 252.5 nm ($E_{1\ cm}^{1\%}$ 310), $\lambda_{inf}$ 291 nm ($E_{1\ cm}^{1\%}$ 139); $[\alpha]_D^{20} +43.5°$ (c 1.0, DMSO).

EXAMPLE 4

(6R,7R)-7-[(Z)-2-(2-Aminothiazol-4-yl)-2-(1-carboxycyclobut-1-oxyimino)acetamido]-3-(4-carbamoyl-1-pyridiniummethyl)-ceph-3-em-4-carboxylate, mono-sodium salt Isonicotinamide (1.22 g) was added to a stirred solution of the product of Example 3 (b) (1.08 g) in water (1.3 ml) containing sufficient sodium bicarbonate to give a final pH of 6.5. Sodium iodide (4 g) was added and the mixture was stirred at 80° C. for 1 hours; sodium bicarbonate was added at intervals to maintain a pH in the range 6.0–6.5. The product was isolated substantially as described in Example 1 (c) to give the title compound, (0.16 g), $[\alpha]_D^{20} -18°$ (c 1.08, H$_2$O); $\lambda_{max}$ (pH 6 buffer) 256 nm ($E_{1\ cm}^{1\%}$ 298), $\lambda_{inf}$ 294 nm ($E_{1\ cm}^{1\%}$ 135).

EXAMPLE 5

(a) t-Butyl (6R,7R) 3-acetoxymethyl-7-[(Z)-2-(2-tritylaminothiazol-4-yl)-2-(1-t-butoxycarbonylcycloprop-1-oxyimino)acetamido]-ceph-3-em-4-carboxylate 1-Hydroxybenzotriazole monohydrate (0.12 g) and dicyclohexylcarbodiimide (0.16 g) were added to a stirred solution of the product of Preparation 7 (0.34 g) and t-butyl (6R,7R)-3-acetoxymethyl-7-aminoceph-3-em-4-carboxylate (0.25 g) in tetrahydrofuran (6 ml). The mixture was stirred at room temperature overnight and then filtered. The filtrate was evaporated. The residue was dissolved in a little ethyl acetate-petroleum ether (bp 60°–80°) (1:1) and eluted through a column of neutral alumina (10 g) with the same solvent. The eluate was concentrated to a foam (0.44 g) which was recrystallized from di-isopropyl ether (15 ml) to give the title compound, (0.29 g), m.pt. 115°–119°; $[\alpha]_D^{20}$ (c 1.0, DMSO) +13°.

(b)
(6R,7R)-3-Acetoxymethyl-7-[(Z)-2-(2-aminothiazol-4-yl)-2-(1-carboxycycloprop-1-oxyimino)acetamido]-ceph-3-em-4-carboxylic acid, hydrochloride salt Concentrated hydrochloric acid (0.6 ml) was added to a stirred solution of the product from Stage (a) (1.92 g) in formic acid (7.5 ml) at 10°. The mixture was stirred at room temperature for 1.25 hours and then filtered. The filtrate was added to di-isopropyl ether (300 ml), and the mixture was stirred for 1.5 hours. The solid was filtered off, washed with di-isopropyl ether and diethyl ether, and dried in vacuo to give the title compound (1.16 g), $[\alpha]_D^{20}$ (c 1.0, DMSO) +35°; $\lambda_{max}$ (pH 6 buffer) 239 nm, ($E_{1\ cm}^{1\%}$ 300).

(c)
(6R,7R)-7-[(Z)-2-(2-Aminothiazol-4-yl)-2-(1-carboxycycloprop-1-oxyimino)acetamido]-3-(1-pyridiniummethyl)ceph-3-em-4-carboxylate, sodium salt A mixture of the product from Stage (b) (0.56 g), sodium bicarbonate (0.17 g), and water (0.5 ml) was warmed to 50°. More sodium bicarbonate (0.09 g) was added, followed by pyridine (0.2 ml). The solution was warmed to 80° and sodium iodide (2 g) was added. The solution was stirred at 80° for 40 minutes, cooled, and diluted with acetone (50 ml). The mixture was filtered, and the solid was washed with acetone and ether to give a solid. This solid was dissolved in water (20 ml) and acidified dropwise with 2 N hydrochloric acid until a precipitate formed which did not redissolve on standing. The mixture was stirred with neutral alumina (5 g) and filtered through a pad of neutral alumina (10 g). The pad was eluted thoroughly with water. The aqueous eluate was concentrated and the residue was triturated with acetone. The solid was filtered and dried to a solid (0.35 g). This solid (0.30 g) was dissolved in a little water and eluted through a column of 50 g Amberlite XAD-2 resin, using first water and then 20% ethanol in water as eluting solvent. The product containing fractions were concentrated, and the residue was triturated with acetone to give the title compound, (0.06 g); $[\alpha]_D^{23}$ 0°±1.5° (c 0.1, water); $\lambda_{max}$ (pH 6 buffer) 254 nm, $(E_{1\ cm}^{1\%}\ 340)$; $\lambda_{inf}$ 296 nm, $(E_{1\ cm}^{1\%}\ 125)$.

EXAMPLE 6

(6R,7R)-7-[(Z)-2-(2-Aminothiazol-4-yl)-2-(1-carboxycyclopent-1-yl-oxyimino)-acetamido]-3-(1-pyridiniummethyl)ceph-3-em-4-carboxylate, dihydrochloride salt Phosphorus pentachloride (0.46 g) was dissolved in methylene chloride (20 ml) at ambient temperature and the solution was cooled to 10°; the product of Preparation 9 (1.095 g) was added in one charge. The mixture warmed to −5° and was stirred for 30 minutes.

The solution was cooled to −10° and triethylamine (0.61 ml) followed by water (6.7 ml) was added with vigorous stirring such that the water did not freeze yet the temperature did not exceed 0°. The two phase mixture was stirred for 3 minutes and transferred to a tap funnel. The lower phase was added to a vigorously stirred suspension of the product of Preparation 10 (a) (0.76 g) in N,N-dimethylacetamide (10 ml) and acetonitrile (10 ml) containing triethylamine (1.4 ml), which had been precooled to −20° and the addition was made such that the temperature did not exceed −10°. The mixture was stirred for 45 minutes at −5° to −10° and was then allowed to warm to 21° over one hour. Methanol (0.3 ml) was added and the methylene chloride was evaporated at reduced pressure with a bath temperature of 30°. The residue was carefully partitioned between ethyl acetate (30 ml) and water (30 ml) and a little sodium chloride added. The organic layer was washed with further water (2×30 ml). The combined washings and further added sodium chloride were extracted with ethyl acetate (20 ml) and the combined organic layers were dried with magnesium sulphate. Evaporation gave a foam (1.79 g) and this was triturated with diisopropyl ether to give a solid (1.35 g).

Most of this solid (1.2 g) was dissolved in formic acid (5 ml) and concentrated hydrochloric acid (0.38 ml) was added with vigorous stirring. After one hour at 21°, the suspension was filtered and the residue was leached with a little formic acid. The combined filtrates were concentrated by evaporation and the residue was triturated with acetone to give the title compound (374 mg) $[\alpha_D + 8.6°$ (c 1.02, H$_2$O) $\lambda_{max}$ (pH 6 buffer) 255 nm (E$_{1\ cm}^{1\%}$289), $\lambda_{infl.}$ 295 (E$_{1\ cm}^{1\%}$273), $\lambda_{infl.}$ 280 (E$_{1\ cm}^{1\%}$158).

EXAMPLE 7

(6R,7R)-7-[(Z)-2-(2-Aminothiazol-4-yl)-2-(2-carboxyprop-2-oxyimino)acetamido]3-(1-pyridiniummethyl)-ceph-3-em-4-carboxylate sodium salt.

(6R,7R)-7-[(Z)-2-(2-Aminothiazol-4-yl)-2-(2-carboxyprop-2-oxyimino) acetamido]-3-(1-pyridiniummethyl)-ceph-3-em-4-carboxylate (2.5 g) was dissolved in water and the solution treated with sodium 2-ethylhexanoate (1.52 g) in methanol (8 ml).

The mixture was added to stirred acetone over 15 minutes, and the suspension obtained filtered, washed and dried to give the title compound (2.5 g); $[\alpha]_D^{23}$ 0° (c 1.0, H$_2$O), $\lambda_{max}$ (pH 6 phosphate), 255 (E$_{1\ cm}^{1\%}$ 327, ε18630) with $\lambda_{infl\ at}$ 240 (E$_{1\ cm}^{1\%}$ 305, ε17,370) and 280 (E$_{1\ cm}^{1\%}$ 172, ε9,800), $\nu_{max}$ (Nujol), 1780 cm$^{-1}$ (β-lactam); sodium, found: 4.5%; calculated for C$_{22}$H$_{21}$O$_7$N$_6$S$_2$ Na: 4.04%.

EXAMPLE 8

(a) Diphenylmethyl (1S,6R,7R)-7-[(Z)-2-(2-t-butoxycarbonylprop-2-oxyimino)-2-(2-tritylaminothiazol-4-yl)-acetamido]-3-bromomethylceph-3-em-1-oxide-4-carboxylate Phosphorus pentachloride (0.75 g) was suspended with stirring in methylene dichloride (20 ml). The mixture was cooled to −10° and the product of Preparation 4 (2.0 g) was added. Stirring was continued at −5° to −10° for 10 minutes. Triethylamine (0.88 ml) in methylene dichloride (5 ml) at −10°, was added, followed after 5 minutes with a suspension of diphenylmethyl (1S,6R,7R)-7-amino-3-bromomethylceph-3-em-1-oxide-4-carboxylate hydrobromide (1.67 g) in methylene dichloride (30 ml) containing triethylamine (0.42 ml), washed in with methylene dichloride (5 ml). The mixture was stirred for 20 minutes at −5° to −10° then poured into half-saturated aqueous sodium bicarbonate solution (50 ml). The organic layer was separated, washed with dilute hydrochloric acid solution (1 N, 3×30 ml) and brine (2×30 ml), and evaporated in vacuo to a foam. The foam was taken up in ethyl acetate (ca 10 ml) and treated with di-isopropyl ether (100 ml). The precipitated solid was collected by filtration, washed with di-isopropyl ether and dried at 40° in vacuo overnight to give the title compound (2.1 g) τ(CDCl$_3$) values include 3.11 (s, —C$\underline{H}$ Ph$_2$), 3.37 (s, thiazol-5-yl proton) 3.88 (dd, J 9 Hz and 5 Hz, 7-H), 5.22+6.02 (Abq-3CH$_2$), 5.49 (d, 5 Hz 6-H), 8.46 (s, CMe$_2$).

(b) (6R,7R)-7-[(Z)-2-(2-Aminothiazol-4-yl)-2-(2-carboxyprop-2-oxyimino) acetamido]-3-(1-pyridiniummethyl)-ceph-3-em-4-carboxylate.

The product of Stage (a) (1 g) was dissolved in acetone (22 ml) and stirred at room temperature. Pyridine (0.08 ml) was added and the mixture was stirred at room temperature for 3 hours. More pyridine (0.72 ml) was added and the mixture was allowed to stand at room temperature overnight. The mixture was poured into stirred diethyl ether (75 ml) and the precipitated solid was collected by filtration, washed with ether and dried at 40° in vacuo. This solid (0.8 g) was redissolved in acetone (22 ml) at −10°. Potassium iodide (0.7 g) was added, followed by acetyl chloride (0.17 ml). The mixture was stirred at −10° for 20 minutes and then more potassium iodide (0.7 g) and acetyl chloride (0.17 ml) were added. After stirring for a further 20 minutes at −10° the mixture was added to a solution of sodium metabisulphite (0.6 g) in water (60 ml) and saturated brine (30 ml). The product was extracted with methylene dichloride (2×50 ml) and the extracts were washed with brine, dried over magnesium sulphate and evaporated under reduced pressure to a foam. This was dissolved in formic acid (6.5 ml) and allowed to stand at room temperature for 15 minutes. Concentrated hydrochloric acid (0.25 ml) was added and the mixture was allowed to stand for a further 1.25 hour. The solid precipitate was filtered and washed with a small quantity of formic acid. The combined filtrate and wash were poured into ethyl acetate (5 ml) and diethyl ether (5 ml) with water (10 ml) and acetonitrile (5 ml). More water was added until two distinct layers were obtained. The lower layer was run off and extracted with diethyl ether (14 ml) containing Amberlite LA2 (7 ml) and acetic acid (0.7 ml). The aqueous layer was again separated and applied to a column of "Zerolit" 225 SRC 15 (H+ form 15 ml). The column was washed with water until neutral. The product was eluted with a 10% solution of pyridine in water. The eluate was evaporated in vacuo to small bulk and treated with acetone. The mixture was cooled to 0° to 40° overnight and filtered. The solid was washed with acetone and dried at 40° in vacuo to give the title compound (0.25 g). The nmr spectrum resembled that of the compound prepared in Example 7.

$\lambda$ max (pH6 phosphate) 255.5 nm ($E_{1cm}^{1\%}$ 374), $\lambda$inf. at 238, ($E_{1cm}^{1\%}$ 340) and 290 nm ($E_{1cm}^{1\%}$ 160).

EXAMPLE 9

(a)

(6R,7R)-7-[(Z)-2-(2-Triphenylmethylaminothiazol-4-yl)-2-(2-t-butoxycarbonylprop-2-oxyimino)acetamido]-3-(1-pyridiniummethyl)-ceph-3-em-4-carboxylate The product of Preparation 4 (3.44 g) was added to a stirred solution of phosphorus pentachloride (1.38 g) in methylene chloride (60 ml), cooled to −10°. The resulting solution was stirred at −5° for 30 minutes, and then cooled to −10°. Triethylamine (1.33 g) was added, followed by water (20 ml). The mixture was stirred for 3 minutes at 0°, when the lower phase was added over 10 minutes to a stirred suspension of the product of Preparation 10(a) (2.19 g), in a mixture of N,N-dimethylacetamide (30 ml)/acetonitrile (30 ml) containing triethylamine (3.03 g), cooled to −10°. The mixture was stirred for 45 minutes at −10° to −5°, followed by 1 hour without cooling. Methanol (1 ml) was added. Methylene chloride was removed by evaporation under reduced pressure. The residual solution was added to water (300 ml) with stirring to precipitate the title compound (4.89 g).

$\tau$(CDCl$_3$) values include 2.78 (s,-[C$_6$H$_5$]$_3$); 3.37 (s-thiazole proton); 0.35, 1.80, 2.12 (pyridinium protons); 4.18 (m, -7-H); 4.95 (6-H); 8.66 (s-t-butyl); 8.50 (s, -C(CH$_3$)$_2$).

(b)

(6R,7R)-7-[(Z)-2-(2-Aminothiazol-4-yl)-2-(2-carboxyprop-2-oxyimino)acetamido]-3-(1-pyridiniummethyl)-ceph-3-em-4-carboxylic aciddihydrochloride The product from Stage (a) (3.38 g) was dissolved in 98% formic acid (20 ml) with stirring. Concentrated hydrochloric acid (1.2 ml) was added, and the mixture was stirred for 1 hour. The precipitated solid was removed by vacuum filtration. Solvent was removed from the filtrate by evaporation under reduced pressure to leave an oil which was triturated with acetone (30 ml) to give the title compound (2.20 g).

$\tau$(D$_2$O/NaHCO$_3$) values include 3.08 (s, -thiazole proton); 1.06, 1.44, 1.93 (pyridinium protons); 4.16 (d, J 5 Hz, 7-H); 4.74 (d,J 5 Hz, 6-H); 8.55 (s,-C(CH$_3$)$_2$).

Acetone by n.m.r., 1 mole.

Water content, 5% (Karl Fischer method).

Chlorine, found 10.1% (C$_{22}$H$_{24}$N$_6$O$_7$S$_2$Cl$_2$+acetone (1 mole)+water (5%) requires Cl, 10.0%).

EXAMPLE 10

(a)

(6R,7R)-7-[(Z)-2-(2-Triphenylmethylaminothiazol-4-yl)-2-(2-t-butoxycarbonylprop-2-oxyimino)acetamido]-3-(1-pyridiniummethyl)-ceph-3-em-4-carboxylate The product from Preparation 10(b) (2.18 g), was reacted as in Example 9(a) to give the title compound (4.03 g), whose spectroscopic properties resembled those of the product of Example 9(a)

(b)

(6R,7R)-7-[(Z)-2-(2-Aminothiazol-4-yl)-2-(2-carboxyprop-2-oxyimino)acetamido]-3-(1-pyridiniummethyl)-ceph-3-em-4-carboxylic acid dihydrochloride The product from Stage (a) (3.8 g) was treated as in Example 9(b) to give the title compound (2.17 g) whose spectroscopic properties resembled those of the product of Example 9(b).

EXAMPLE 11

(a) (6R,7R)-7-[(Z)-2-(2-triphenylmethylaminothiazol-4l-yl)-2-(1-t-butoxycarbonylcyclobut-1-oxyimino)acetamido]-3-(1-pyridiniummethyl)ceph-3-em-4-carboxylate Phosphorus pentachloride (1.38 g) was dissolved in 60 ml of dichloromethane. The solution was cooled to −10° and the product of Preparation 6 (3.48 g) was added in one charge. The solution was stirred at −5° for 30 minutes. Triethylamine (1.8 ml) was added, followed by water (20 ml). The mixture was stirred at 0° C. for 3 minutes. The lower phase was then added to a pre-cooled mixture of the product of Preparation 10(a) (2.18 g) in dimethylacetamide (30 ml) and acetonitrile (30 ml) with triethylamine (4.2 ml) added at −10° C.

The reaction mixture was stirred for 45 minutes between −5° C. and −10° C. Cooling was then removed and the reaction was stirred for a further hour, ambient temperature being attained during this time. The solvent was removed under reduced pressure and the residue partitioned between ethyl acetate and water. The organic phase was washed with brine and the combined aqueous extracts extracted with ethyl acetate. The combined ethyl acetate extracts were dried in the presence of charcoal and the solvent was removed under reduced pressure. The residue was triturated with isopropyl ether to give the title compound (3.80 g).

$\nu$max (Nujol) 1780 cm$^{-1}$ ($\beta$-lactam); $\tau$(CDCl$_3$) values include 2.74 (s, triphenylmethyl); 8.66 (s, t-butyl)

(b)

(6R,7R)-7-[(Z)-2-(2-aminothiazol-4-yl)-2-(1-carboxycyclo-but-1-oxyimino)acetamido]-3-(1-pyridiniummethyl)ceph-3-em-4-carboxylic acid dihydrochloride The product from Stage (a), (2.57 g) was stirred at ambient temperature in a mixture of 98% formic acid (15 ml), and concentrated hydrochloric acid (0.9 ml) for one hour. The mixture was then filtered and the solvent removed under reduced pressure. The resulting residue was triturated with acetone to produce the title compound (1.79 g).

$\nu$max (Nujol) 1785 cm$^{-1}$ ($\beta$-lactam); $\tau$values (D$_2$O+NaHCO$_3$) include 1.05, 1.42, 1.91; (m, pyridinium protons), 3.01 (s, aminothiazole proton); 4.13 (d, J 5

Hz, C$_7$ proton), 4.68 (d, J 5 Hz, C-6 proton); 7.4–8.4 (broad m, cyclobutyl protons).

Dimethylacetamide ($\frac{1}{3}$ mole) and acetone ($\frac{1}{2}$ mole) by n.m.r.

Water content 7.4% (Karl Fischer method).

Chlorine, found 9.2% (C$_{23}$H$_{24}$N$_6$O$_7$S$_2$Cl$_2$+$\frac{1}{3}$ mole dimethylacetamide+$\frac{1}{2}$ mole acetone+7.4% water requires Cl, 9.5%).

EXAMPLE 12

(a)

(6R,7R)-3-Acetoxymethyl-7-[(Z)-2-(2-aminothiazol-4-yl)-2-(2-carboxyprop-2-oxyimino)-acetamido]-ceph-3-em-4-carboxylic Acid Hydrochloride The product of Example 1(a) (200 g) was dissolved in formic acid (800 ml) pre-cooled to +10° and concentrated hydrochloric acid (60 ml) was added over 5 minutes to the stirred mixture. Stirring was continued at 20° to 22° for 1$\frac{1}{4}$ hours before cooling to +10° and filtering. The bed was washed with formic acid (30 ml). The combined filtrate and wash were concentrated by evaporation at 20° to a yellow foam which was triturated with ethyl acetate (800 ml). The solid which deposited was collected by filtration, washed with ethyl acetate (200 ml) and dried in vacuo at room temperature overnight to give the title compound (124.6 g) $\lambda_{max}$ (ethanol) 234.5 nm, E$_{1cm}^{1\%}$ 311.

(b)

(6R,7R)-7-[(Z)-2-(2-Aminothiazol-4-yl)-2-(2-carboxyprop-2-oxyimino)acetamido]-3-(pyridinium-1-ylmethyl)ceph-3-em-4-carboxylate Hydrate The product from Stage (a) (40 g) was added to a stirred mixture of water (40 ml) and pyridine (25.6 ml) followed by sodium iodide (160 g) and the mixture heated at 60° for 3$\frac{1}{2}$ hours. The hot solution was poured into stirred acetone (2 l) and diluted with diethyl ether (1.2 l). The suspension was cooled to 2° and the crude product collected by filtration (50.65 g). This was dissolved in water (480 ml) and stirred with formic acid (19.3 ml), 'Amberlite LA2' (280 ml) in ether (560 ml). The mixture was separated and the organic layer washed twice with water (240 ml each). The aqueous layers were washed with ether (280 ml) and applied to a column of 'Zerolit 225, SRC 15' (200 ml H+) followed by distilled water until the eluate was neutral. The column was eluted with 10% pyridine in water and the eluate passed through a column of neutral alumina (40 g). The eluate was evaporated to a syrup under reduced pressure and the syrup added dropwise to stirred acetone (500 ml). The title compound (13.09 g) was obtained by filtration and equilibration in air. H$_2$O, 7.0% (Karl Fischer); $\lambda_{max}$ 255 nm (E$_{1cm}^{1\%}$ 364) $\lambda_{infl}$ 243 and 285 nm (E$_{1cm}^{1\%}$ 338 and 171), [$\alpha$]$_D^{20}$ −3° (pH 6 phosphate buffer).

EXAMPLE 13

(a)

(6R,7R)-7-[(Z)-2-(2-Tritylaminothiazol-4-yl)-2-(2-t-butoxycarbonylprop-2-oxyimino)acetamido]-3-(1-pyridiniummethyl)ceph-3-em-4-carboxylate, N,N-dimethylformamide Solvate Finely powdered product of Example 9(a) was added to stirred N,N-dimethylformamide (15 ml) at 23°. The solid dissolved and shortly thereafter crystallisation occurred. The stirred mixture was diluted by dropwise addition of diisopropyl ether (20 ml). The solid was collected by filtration to give the title compound (3.06 g) as colourless meedles.

N,N-dimethylformamide by nmr=2$\frac{1}{2}$ moles.

$\tau$(DMSO-d$_6$): 2.4–3.0 (m, trityl); 3.32 (s, aminothiazole ring proton); 0.47, 1.38, 1.82 (pyridinium protons); 4.34 (m, C-7 proton); 4.92 (d, J-5, C-6 proton); 8.64 (s, t-butyl protons); 8.62 (s, (CH$_3$)$_2$-C<), [$\alpha$]$_D^{20}$= −27.5° (C=1.1 in methanol).

(b)

(6R,7R)-7-[(Z)-2-(2-Aminothiazol-4-yl)-2-(carboxyprop-2-oxyimino)-acetamido]-3-(1-pyridiniummethyl)-ceph-3-em-4-carboxylic Acid Dihydrochloride The product from Stage (a) (2.1 g) was dissolved in formic acid (10 ml) at 22°. Concentrated hydrochloric acid (0.8 ml) was added and after 75 minutes, the precipitated solid was filtered off. The filtrate was evaporated and industrial methylated spirits (10 ml) was added. The solution was re-evaporated. The residue was dissolved in methanol and the solution added to diisopropyl ether, giving the title compound, (1.35 g) [$\alpha$]$_D^{20}$ −14.7° (c=0.95 in pH 6 buffer) $\tau$ (DMSO-d$_6$)

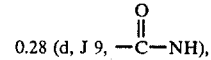

0.28 (d, J 9, —C—NH), 0.77 (d, J 6), 1.25 (t, J 6), 1.70 (t, J 6, pyridinium ring protons); 3.0 (s, aminothiazole protons); 3.99 (d d, J 9.5, 7-H); 4.67 (d, J 5, 6-H); 8.42 (s, -(CH$_3$)$_2$).

PHARMACY EXAMPLES

Example A - Dry Powder for Injection

Formula Per Vial

| | |
|---|---|
| (6R,7R)-7-[(Z)-2-(2-Aminothiazol-4-yl)-2-(2-carboxyprop-2-oxyimino) acetamido]-3-(1-pyridiniummethyl)ceph-3-em-4-carboxylate. | 500 mg |
| Lysine Acetate | 189 mg |

Method

The cephalosporin antibiotic was blended with lysine acetate and filled into a glass vial. The vial headspace was purged with nitrogen and a combination seal applied by crimping. The product was dissolved, as for administration, by the addition of 2 ml Water for injections.

Example B - Dry Powder for Injection

Fill sterile (6R,7R)-7-[(Z)-2-(aminothiazol-4-yl)-2-(2-carboxyprop-2-oxyimino)acetamido]-3-(1-pyridiniummethyl)ceph-3-em-4-carboxylate, monosodium salt into glass vials such that each vial contains an amount equivalent to 1.0 g of the antibiotic acid. Carry out the filling aseptically under a blanket of sterile nitrogen. Close the vials using rubber disks or plugs, held in position by aluminium overseals, thereby preventing gaseous exchange or ingress of micro-organisms. Reconstitute the product by dissolving in Water for Injections or other suitable sterile vehicle shortly before administration.

Example C - Injection Twin-Pack (a) Fill 500 mg quantities of sterile (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate aseptically into glass vials under a blanket of sterile nitrogen. Close the vials using rubber disks or plugs, held in position by aluminium overseals, thereby preventing gaseous exchange or ingress of microorganisms.

(b) Prepare a 3.84% w/v solution of sodium bicarbonate, clarify by filtration and fill 2.15 ml into clean ampoules. Pass carbon dioxide into the contents of each ampoule for one minute before sealing. Sterilise the ampoules by autoclaving and check for clarity.

(c) Reconstitute the cephalosporin antibiotic shortly before administration by dissolving in 2.0 ml of the sodium bicarbonate solution.

Example D - Dry Powder for Injection

Formula Per Vial

| | |
|---|---|
| (6R,7R)-7-[(Z)-2-(2-Aminothiazol-4-yl)-2-(1-carboxycyclobut-1-oxyimino)acetamido]-3-(1-pyridiniummethyl)ceph-3-em-4-carboxylate | 500mg |
| sodium carbonate, anhydrous | 47mg |

Method

The cephalosporin antibiotic was blended with sodium carbonate and filled into a glass vial. The vial headspace was purged with nitrogen and a combination seal applied by crimping. The product was dissolved, as for administration, by the addition of 2 ml Water for Injections.

Example E - Injection for Veterinary Use

Formula

| | |
|---|---|
| (6R,7R)-7-[(Z)-2-(2-Aminothiazol-4-yl)-2-(1-carboxycyclobut-1-oxyimino)acetamido]-3-(1-pyridiniummethyl)ceph-3-em-4-carboxylate | 10% w/v |
| Aluminium distearate 2% w/v | to 100% w/v |
| Ethyl Oleate to 100% w/v | |

Method

Disperse the aluminum distearate in ethyl oleate, heat at 150° C. for one hour with stirring and cool to room temperature. Add the sterile milled antibiotic aseptically to the vehicle and refine with a high speed mixer. Fill the product aseptically into injection vials and close with rubber seals or plugs held in position by aluminium overseals.

We claim:

1. A cephalosporin antibiotic compound which is (6R,7R)-7-[(Z)-2-(2-aminothiazol-4-yl)-2-(2-carboxyprop-2-oxyimino)acetamido]-3-(1-pyridiniummethyl)-ceph-3-em-4-carboxylate or a non-toxic salt thereof.

2. A non-toxic salt of the compound of claim 1.

3. The mono-sodium salt of the compound of claim 1.

4. The compound of claim 1 which is (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate.

5. A pharmaceutical composition for use in human or veterinary medicine comprising an effective amount of an antibiotic compound of claim 1 in association with a pharmaceutical carrier or excipient.

6. A method of combatting bacterial infection in a human or an animal comprising administering an antibacterially effective amount of a compound of claim 1.

* * * * *

UNITED STATES PATENT AND TRADEMARK OFFICE
CERTIFICATE OF CORRECTION

PATENT NO. : 4,258,041

DATED : March 24, 1981

INVENTOR(S) : Cynthia H. O'Callaghan; David G. H. Livermore; Christopher E. Newall It is certified that error appears in the above—identified patent and that said Letters Patent is hereby corrected as shown below:

IN THE TITLE PAGE:

Item [51], please delete "499/44" and insert --501/46--.
Item [56], line 5 under U.S. PATENT DOCUMENTS, please delete "4,032,950" and insert --4,033,950--;
line 10 under U.S. PATENT DOCUMENTS, please delete "3/1978" and insert --5/1978--;
line 1 under FOREIGN PATENT DOCUMENTS, please delete "10/1970" and insert --10/1978--;
line 1 under OTHER PUBLICATIONS, please delete "Tsochiya" and insert --Tsuchiya--;
line 2 under OTHER PUBLICATIONS, please delete "557-560" and insert --557-568--;
line 5 under OTHER PUBLICATIONS, please delete "C. F." and insert --C. R.--;
line 10 under OTHER PUBLICATIONS, please delete "Hem. Pharm. Bull. 25, (11), 3115-3118, (1977)" and insert --Chem. Pharm. Bull. 25, (11), 3115-3119, (1977).

IN THE ABSTRACT

Line 16, counting the general formula (I) as one line, please delete "ceph-3-em-4 carboxylate" and insert --ceph-3-em-4-carboxylate--.

UNITED STATES PATENT AND TRADEMARK OFFICE
CERTIFICATE OF CORRECTION

PATENT NO. : 4,258,041

DATED : March 24, 1981

INVENTOR(S) : Cynthia H. O'Callaghan; David G. H. Livermore; Christopher E. Newall It is certified that error appears in the above—identified patent and that said Letters Patent is hereby corrected as shown below:

Column 2, line 43, please delete "described" and insert --describes--.
Column 6, line 27, please delete "lable" and insert --labile--.
Column 8, line 34, please delete "B is <S" and insert --B is >S--.
Column 9, line 8, please delete "N,ethyl" and insert --N-ethyl--.
Column 14, line 14, please delete "ter-solubity" and insert --ter-solubility--;
line 52, please delete "M=multiplet" and insert --m=multiplet--.
Column 20, line 26, please delete "dicyclohexylcarbodimide" and insert --dicyclohexylcarbodiimide--.
Column 24, line 25, please delete "41" and insert --4--.
Column 26, line 44, please delete "cephalospirin" and insert --cephalosporin--;
line 48, please delete "injec-" and insert --Injec---.

Signed and Sealed this

Sixth Day of October 1981

[SEAL]

Attest:

GERALD J. MOSSINGHOFF

Attesting Officer　　Commissioner of Patents and Trademarks

UNITED STATES PATENT AND TRADEMARK OFFICE

CERTIFICATE EXTENDING PATENT TERM
UNDER 35 U.S.C. 156

Patent No.     : 4,258,041

Dated          : Mar. 24, 1981

Inventor(s)    : Cynthia H. O'Callaghan, et al

Patent Owner   : Glaxo Group Limited

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

483 DAYS with all rights pertaining thereto as provided by 35 USC 156(b).

I have caused the seal of the Patent and Trademark Office to be affixed this Third day of September 1986.

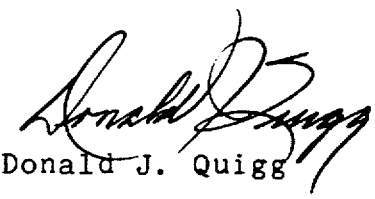

Donald J. Quigg

Assistant Secretary and Commissioner of Patents and Trademarks